(12) United States Patent
Hickle

(10) Patent No.: US 7,539,537 B2
(45) Date of Patent: May 26, 2009

(54) SYSTEMS AND METHODS FOR PROVIDING SENSOR FUSION

(75) Inventor: Randall S. Hickle, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 393 days.

(21) Appl. No.: 10/677,481

(22) Filed: Oct. 3, 2003

(65) Prior Publication Data
US 2004/0111014 A1    Jun. 10, 2004

Related U.S. Application Data

(60) Provisional application No. 60/415,523, filed on Oct. 3, 2002.

(51) Int. Cl.
*A61B 5/00*    (2006.01)
*A61M 31/00*    (2006.01)

(52) U.S. Cl. ........................... 600/544; 604/66

(58) Field of Classification Search .......... 600/300–301
See application file for complete search history.

(56) References Cited

U.S. PATENT DOCUMENTS

| | | |
|---|---|---|
| 2,185,068 A | 12/1939 | Sholes et al. |
| 2,225,201 A | 12/1940 | Anderson |
| 2,690,178 A | 9/1954 | Bickford |
| 2,888,922 A | 6/1959 | Bellville |
| 1,176,476 A | 3/1961 | Jones |
| 3,143,111 A | 8/1964 | Green |
| 3,651,806 A | 3/1972 | Hirshberg |
| 3,762,398 A | 10/1973 | Schefke et al. |
| 3,898,983 A | 8/1975 | Elam |
| 4,078,562 A | 3/1978 | Friedman |
| 4,080,966 A | 3/1978 | McNally et al. |
| 4,148,312 A | 4/1979 | Bird |
| 4,275,727 A | 6/1981 | Keeri-Szanto |
| 4,280,494 A | 7/1981 | Cosgrove, Jr. et al. |
| 4,308,866 A | 1/1982 | Jelliffe et al. |
| 4,392,849 A | 7/1983 | Petre et al. |
| 4,533,346 A | 8/1985 | Cosgrove, Jr. et al. |
| 4,550,726 A | 11/1985 | McEwen |
| 4,551,133 A | 11/1985 | Zegers de Beyl et al. |

(Continued)

FOREIGN PATENT DOCUMENTS

JP    04-309362    10/1992

(Continued)

OTHER PUBLICATIONS

PCT International Search Report dated Apr. 9, 2004 for International Application No. PCT/US03/31906.

(Continued)

*Primary Examiner*—Robert L Nasser
(74) *Attorney, Agent, or Firm*—Hogan & Hartson LLP

(57) ABSTRACT

The present invention comprises a system that incorporates the natural relationships of patient parameters into a medical monitoring system in order to increase monitoring specificity by reducing false positive alarms resulting from spurious data and inconclusive data. The invention also comprises a system that incorporates the natural relationships of patient parameters in order to use the data obtained from those parameters to non-invasively monitor a patient parameter that typically precludes direct monitoring.

21 Claims, 7 Drawing Sheets

U.S. PATENT DOCUMENTS

| | | | |
|---|---|---|---|
| 4,610,254 | A | 9/1986 | Morgan et al. |
| 4,634,426 | A | 1/1987 | Kamen |
| 4,681,121 | A | 7/1987 | Kobal |
| 4,688,577 | A | 8/1987 | Bro |
| 4,718,891 | A | 1/1988 | Lipps |
| 4,731,051 | A | 3/1988 | Fischell |
| 4,756,706 | A | 7/1988 | Kerns et al. |
| 4,871,351 | A | 10/1989 | Feingold |
| 4,942,544 | A | 7/1990 | McIntosh et al. |
| 5,046,491 | A | 9/1991 | Derrick |
| 5,065,315 | A | 11/1991 | Garcia |
| 5,088,981 | A | 2/1992 | Howson et al. |
| 5,094,235 | A | 3/1992 | Westenskow et al. |
| 5,183,038 | A | 2/1993 | Hoffman et al. |
| 5,231,981 | A | 8/1993 | Schreiber et al. |
| 5,258,906 | A | 11/1993 | Kroll et al. |
| 5,262,944 | A | 11/1993 | Weisner et al. |
| 5,286,252 | A | 2/1994 | Tuttle et al. |
| 5,309,908 | A | 5/1994 | Friedman et al. |
| 5,352,195 | A | 10/1994 | McEwen |
| 5,432,698 | A | 7/1995 | Fujita |
| 5,445,621 | A | 8/1995 | Poli et al. |
| 5,507,277 | A | 4/1996 | Rubsamen et al. |
| 5,522,798 | A | 6/1996 | Johnson et al. |
| 5,555,891 | A | 9/1996 | Eisenfeld |
| 5,558,638 | A | 9/1996 | Evers et al. |
| 5,614,887 | A | 3/1997 | Buchbinder |
| 5,630,710 | A | 5/1997 | Tune et al. |
| 5,653,739 | A | 8/1997 | Maurer et al. |
| 5,676,133 | A | 10/1997 | Hickle et al. |
| 5,677,290 | A | 10/1997 | Fukunaga |
| 5,713,856 | A | 2/1998 | Eggers et al. |
| 5,724,025 | A * | 3/1998 | Tavori ..................... 340/573.1 |
| 5,730,140 | A | 3/1998 | Fitch |
| 5,733,259 | A | 3/1998 | Valcke et al. |
| 5,795,327 | A | 8/1998 | Wilson |
| 5,873,369 | A | 2/1999 | Laniado et al. |
| 5,882,338 | A | 3/1999 | Gray |
| 5,954,050 | A | 9/1999 | Christopher |
| 5,957,885 | A | 9/1999 | Bollish et al. |
| 5,980,501 | A | 11/1999 | Gray |
| 6,062,216 | A | 5/2000 | Corn |
| 6,099,481 | A * | 8/2000 | Daniels et al. .............. 600/538 |
| 6,152,130 | A | 11/2000 | Abrams et al. |
| 6,158,430 | A | 12/2000 | Pfeiffer et al. |
| 6,165,151 | A | 12/2000 | Weiner |
| 6,165,154 | A | 12/2000 | Gray et al. |
| 6,182,667 | B1 | 2/2001 | Hanks et al. |
| 6,186,977 | B1 | 2/2001 | Andrews et al. |
| 6,289,238 | B1 | 9/2001 | Besson et al. |
| 6,302,844 | B1 | 10/2001 | Walker et al. |
| 6,305,372 | B1 | 10/2001 | Servidio |
| 6,305,373 | B1 | 10/2001 | Wallace et al. |
| 6,579,242 | B2 | 6/2003 | Bui et al. ..................... 600/537 |
| 6,629,933 | B1 | 10/2003 | Lindner ..................... 600/532 |
| 2003/0120164 | A1 * | 6/2003 | Nielsen et al. ............. 600/513 |
| 2003/0125662 | A1 * | 7/2003 | Bui ............................. 604/67 |
| 2005/0182355 | A1 * | 8/2005 | Bui ............................. 604/66 |

FOREIGN PATENT DOCUMENTS

| | | |
|---|---|---|
| WO | 97/00092 | 1/1997 |
| WO | 97/07838 | 3/1997 |
| WO | 97/34648 | 9/1997 |
| WO | 98/10701 | 3/1998 |
| WO | 99/62403 | 12/1999 |

OTHER PUBLICATIONS

J. Gray et al., Development of the Technology for 'Diprifusor' TCI Systems, Anesthesia, 1998, 53, Supplemental 1, pp. 22-27.

Michel M. R. F. Struys, et al. "Comparison of Closed-Loop Controlled Administration of Propofol Using Bispectral Index as the Controlled Variable versus 'Standard Practice' Controlled Administartion," Anesthesiology, 95:6-17 (2001).

E. Mortier et al., "Closed-Loop Controlled Administration of Propoful Using Bispectral Analysis," Anaesthesia, 53:749-754 (1998).

J. B. Glen et al., "The Development of 'Diprifusor': A TCI System for Propofol," Anaesthesia, 53(1):13-21 (1998).

G. N. C. Kenny et al., "Closed-Loop Control of Propofol Anaesthesia," British J. of Anaesthesia, 83(2):223-228 (1999).

"A New Level of Control for Faster, More Predictable Recovery," BIS, Your Guide to the Hypnotic State During Anesthesia and Sedation.

P. Glass et al., "Intravenous Drug Delivery Systems," Anesthesia, pp. 389-416.

* cited by examiner

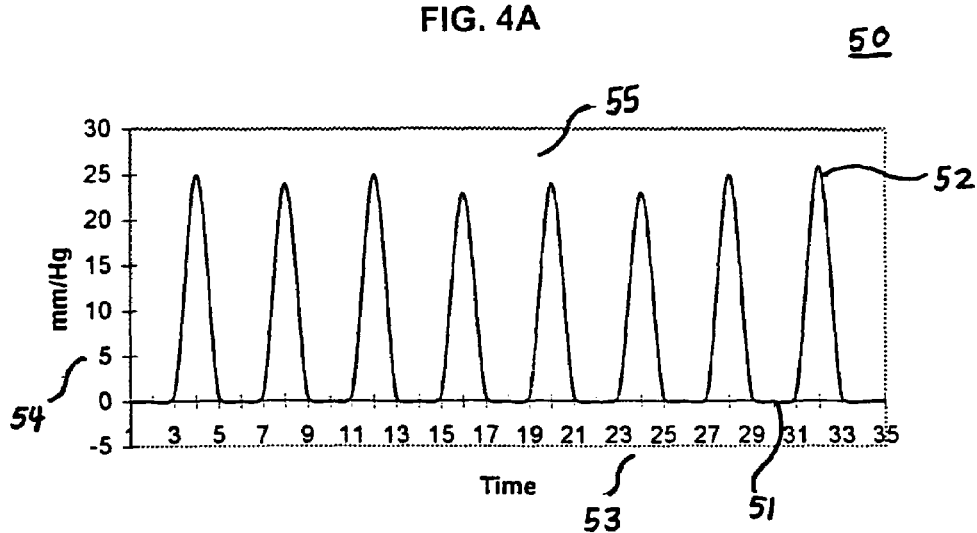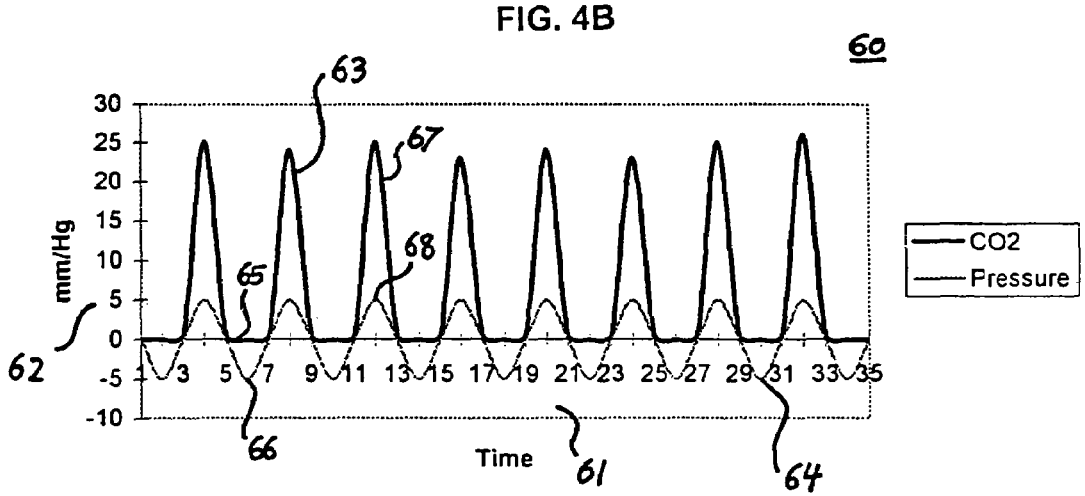

SYSTEMS AND METHODS FOR PROVIDING SENSOR FUSION

CROSS REFERENCE TO RELATED APPLICATIONS

This application claims priority under 35 U.S.C. §119(e) to U.S. Provisional Patent Application No. 60/415,523, "Systems and Methods for Providing Sensor Fusion," filed Oct. 3, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates, in general, to sensor fusion and, more particularly, to sensor fusion in medical devices incorporating multiple monitors of multiple patient parameters.

2. Description of the Related Art

Spurious monitored data may cause systems that rely on them to take potentially hazardous action, to fail to take action in critical situations, or to alarm unnecessarily. For example, a sedation and analgesia system may be monitoring a patient's heart rate with an electrocardiograph (ECG) when the ECG becomes erratic. Based on the single monitor, the sedation and analgesia system may signal an alarm indicating, for example, a dangerously low heart rate, when the erratic ECG data is actually spurious. A high frequency of these false positive alarms may annoy clinicians and may result in less attention being given to truly life-threatening conditions.

Sensor fusion is herein defined as the analysis of monitored data and information from at least one sensor, given a first patient parameter, along with data from at least one other sensor, given a second patient parameter, in order to increase the sensitivity and specificity of parameters defining a patient state. A highly sensitive system ensures that system ensures that when a truly critical event occurs, that event is not missed. In a highly specific system, when an alarm does sound, the alarm is representative of a truly critical situation and is not based on spurious data. Providing a single monitor, such as an ECG, to monitor heart rate may result in a sedation and analgesia system having a low specificity where, for example, a clinician's motion in the surgical field can add disruptive electrical activity that the ECG may interpret as ventricular fibrillation. Without any means of verifying the data presented by the ECG, the monitor would alarm to alert the attending clinician of a potentially life threatening situation even though the data may be spurious.

Monitoring problems may also arise when monitors such as, for example, capnometers, provide inconclusive evidence regarding patient condition. Air brought into the lungs during inhalation typically carries a negligible amount of carbon dioxide due to the nominal concentration of the gas in the atmosphere. As atmospheric air passes into the lungs it will participate in gas transfer across alveolar membranes, where oxygen is taken into the blood and carbon dioxide is excreted for removal from the body. The eliminated carbon dioxide is commonly used by capnometers to ascertain a patient's respiratory rate, to determine whether they are experiencing sufficient gas exchange, and for other ventilatory reasons. When monitored with capnometry, a healthy patient breathing normally will produce a capnogram with a series of waveforms. The peak of each waveform is known as the end-tidal carbon dioxide (EtCO2) level. The peak at the end of each exhalation is generally most representative of the gas exchange occurring at the alveolar level where gases expired at the end of exhalation have been held for the longest portion of time in the deepest portions of the lungs where alveolar gas exchange takes place. Thus, end-tidal carbon dioxide is clinically interpreted as representing the patient's blood level of carbon dioxide, the trend of which reflects the patient's ventilatory state over time.

During inhalation, a nominal capnometry waveform can then generally be seen as a period of negligible carbon dioxide during inhalation (due to the low atmospheric gas concentration) followed by a second period of negligible carbon dioxide during the beginning of exhalation (where gas is expelled from upper regions of the respiratory tract that do not participate in gas exchange). Following inhalation and the beginning of exhalation, the waveform indicating carbon dioxide levels will rise sharply before beginning to plateau and finally peaking at the end of exhalation at the EtCO2. Following exhalation, the carbon dioxide levels will drop sharply to a negligible level as inhalation begins once again.

Though capnometers are commonly used and are useful in ascertaining the above-mentioned patient parameters, it may be difficult to differentiate, using only capnometry, between hyperventilation (often a non-critical issue) and hypoventilation (a highly critical and potentially life-threatening condition.) Hyperventilation is generally characterized by shallow, fast, short breaths, where capnometers will show a dramatic decrease in expired carbon dioxide as the patient's hyperventilatory state serves to deplete the blood stores of carbon dioxide.

Hypoventilation is generally characterized by depressed respiration, where hypoventilation may be caused by, for example, drug overdose and airway obstruction. Although the underlying patient physiology is entirely different in hypoventilation compared to hyperventilation, the condition can look surprisingly similar to a capnometer. Like hyperventilation, hypoventilation caused by partial or complete airway obstruction will often also register as a series of diminished capnography waveforms and a low level of end-tidal carbon dioxide. In the case of hypoventilation, the diminished capnography waveforms are caused by inadequate exhalation of air past the airway obstruction. Since the capnometry waveforms of both hyperventilation and hypoventilation patient states can appear very similar, when monitoring is done solely by capnometry, there is no choice in monitoring algorithms but to alarm in either patient state in order to avoid potentially missing a life-threatening hypoventilation event. However, such a system may also result in frequent false positive alarms based on the benign condition of hyperventilation.

Though patient parameters such as heart rate, capnometry, pulse oximetry, blood pressure, and others are generally monitored separately when determining patient condition, such parameters often have underlying physiological dependencies and correlations that allow for information about one to be gathered by monitoring another. For example, heart rate as monitored by an electrocardiograph (ECG) is physiologically related to pulse oximetry monitoring. The electrical activation of the ventricles illustrates the major waveform (QRS) detected on the ECG, in a one-to-one ratio with the plethysmogram, representing a pulsatile wave of blood motion under the pulse oximeter's monitored site. When the two waveforms are compared, the QRS portion of the ECG generally occurs a few milliseconds before a pulse in the plethysmogram waveform. If a severe disruption of cardiac output occurs, such as that associated with ventricular fibrillation, the plethysmogram will no longer correlate one-to-one with the ECG and will be irregular. Therefore, if an ECG reading indicates that a potentially life-threatening patient event is occurring, the plethysmogram will likely also indicate such a negative event. If the information from these two disparate monitors is processed together, the output can significantly increase the specificity of alarm algorithms. Furthermore, if the ECG becomes erratic due to, for example, clinician motion in the surgical field, the plethysmogram will likely remain regular, whereupon it may be inferred that the irregular ECG is spurious and not the result of a truly life-threatening patient event.

Often, there are patient parameters that are difficult to measure due to their invasiveness into the human body, yet may serve as beneficial indicators of a patient's condition. For example, systemic vascular resistance (SVR), if measured directly, may require the insertion of an uncomfortable monitoring device into the patient's blood vessels. Such an invasive procedure may preclude clinicians from using such a monitoring device, where potentially important information related to a patient's cardiovascular or hemodynamic condition will go unmonitored.

SUMMARY OF THE INVENTION

The present invention comprises a system that incorporates the natural relationships of patient parameters, such as heart rate and pulse oximetry, into a medical monitoring system in order to increase monitoring specificity by reducing false positive alarms resulting from spurious data and inconclusive data. The invention also comprises a system that incorporates the natural relationships of patient parameters in order to use the data obtained from those parameters to non-invasively monitor a patient parameter that typically precludes direct monitoring. This system includes a controller programmed to automatically control the monitoring and comparison of the parameters in order to increase system specificity and reduce clinician workload.

The present invention thus comprises a monitoring system that has increased specificity by detecting data artifacts from monitors, such as capnometers, while still retaining sensitivity in detecting the incidence of conditions such as hypoventilation. The system of the present invention incorporates the natural relationship between patient parameters in order to increase the specificity of the system and to decrease the probability of false positive alarm responses. The invention also comprises the monitoring of patient parameters that generally precludes direct monitoring, such as SVR, in a way that is both accurate and comfortable for the patient.

BRIEF DESCRIPTION OF THE DRAWINGS

FIG. 4A illustrates one embodiment of a capnogram illustrating a carbon dioxide partial pressure waveform that is representative of data utilized by the present invention;

FIG. 4B illustrates a further embodiment of a capnogram illustrating a carbon dioxide partial pressure waveform that is representative of data utilized by the present invention;

DETAILED DESCRIPTION OF THE INVENTION

Figure 1:
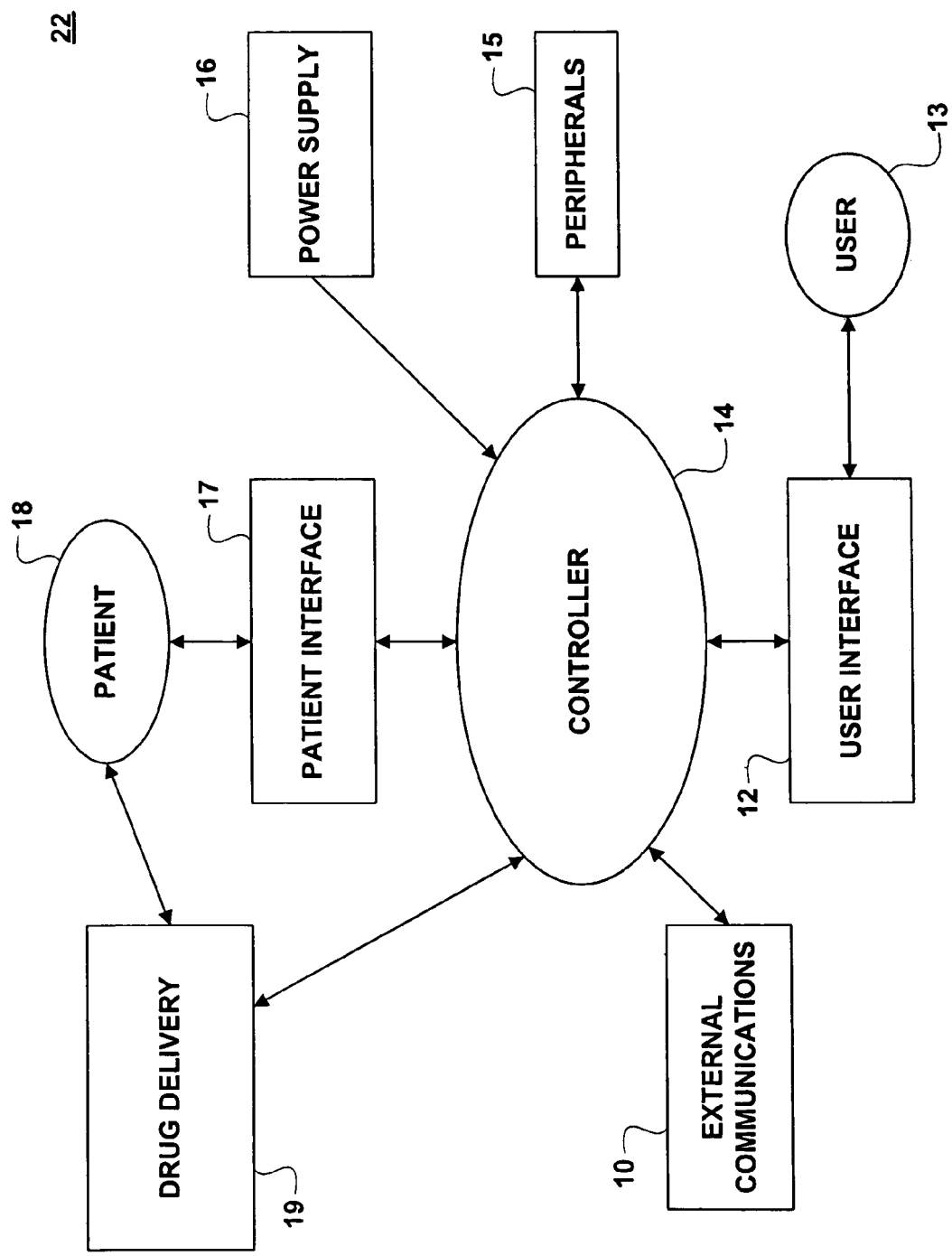
FIG. 1 illustrates a block diagram depicting a representative system for sedation and analgesia in which the present invention can be incorporated.

FIG. 1 illustrates a block diagram depicting a representative system in which the present invention can be incorporated. Sedation and analgesia system 22 includes user interface 12, software controlled controller 14, peripherals 15, power supply 16, external communications 10, pressure delivery 11, patient interface 17, and drug delivery 19, where sedation and analgesia system 22 is operated by user 13 in order to provide sedation and/or analgesia to patient 18. An example of sedation and analgesia system 22 is disclosed and enabled by U.S. patent application Ser. No. 09/324,759, filed Jun. 3, 1999 and incorporated herein by reference in its entirety. While sedation and analgesia system 22 is a representative system, the present invention can be incorporated in any system that can benefit from the incorporation of the natural relationships of patient parameters into a medical monitoring system.

In the representative system of FIG. 1, patient interface 17 includes two or more patient health monitors (not shown) such as vital signs monitors and consciousness monitors including, but not limited to, non-invasive blood pressure monitors, pulse oximeters, capnometers, ECGs, patient consciousness assessment systems, ventilatory flow monitors, ventilatory pressure monitors, impedance plethysmographs (IPGs), gas analyzers, ventilatory temperature monitors, ventilatory humidity monitors, and acoustical monitors. The patient monitors of patient interface 17 may be electronically coupled to controller 14 and provide signals representing the patient's actual physiological condition. In one embodiment of the present invention, at least one monitor monitors a first patient parameter while at least one other monitor monitors a second related patient parameter, where the first patient parameter and the second patient parameter are related.

By providing sensor fusion of the two monitors, where the monitored data of the first patient parameter is analyzed with the data from the second related patient parameter, sedation and analgesia system 22 increases its specificity by diminishing the effects of spurious data and qualifying inconclusive data that would have been possible if either patient parameter was monitored independently of the other. This sensor fusion may further increase system sensitivity, where critical situations missed by a first sensor may be detected by the sensors monitoring related patient parameters. Controller 14 may compare the electronic output from patient interface 17 with data stored in a memory device, where such data may represent sets of one or more safe and undesirable patient physiological condition parameter comparisons such as, for example, a safe and undesirable relationships between an ECG and plethysmogram as monitored by a pulse oximeter. These sets of data are collectively referred to as a safety data set. Based on the comparison, controller 14 may command a conservative application of drug delivery and/or other suitable effectors in accord with such parameters at safe, cost-effective optimized values.

Figure 2:
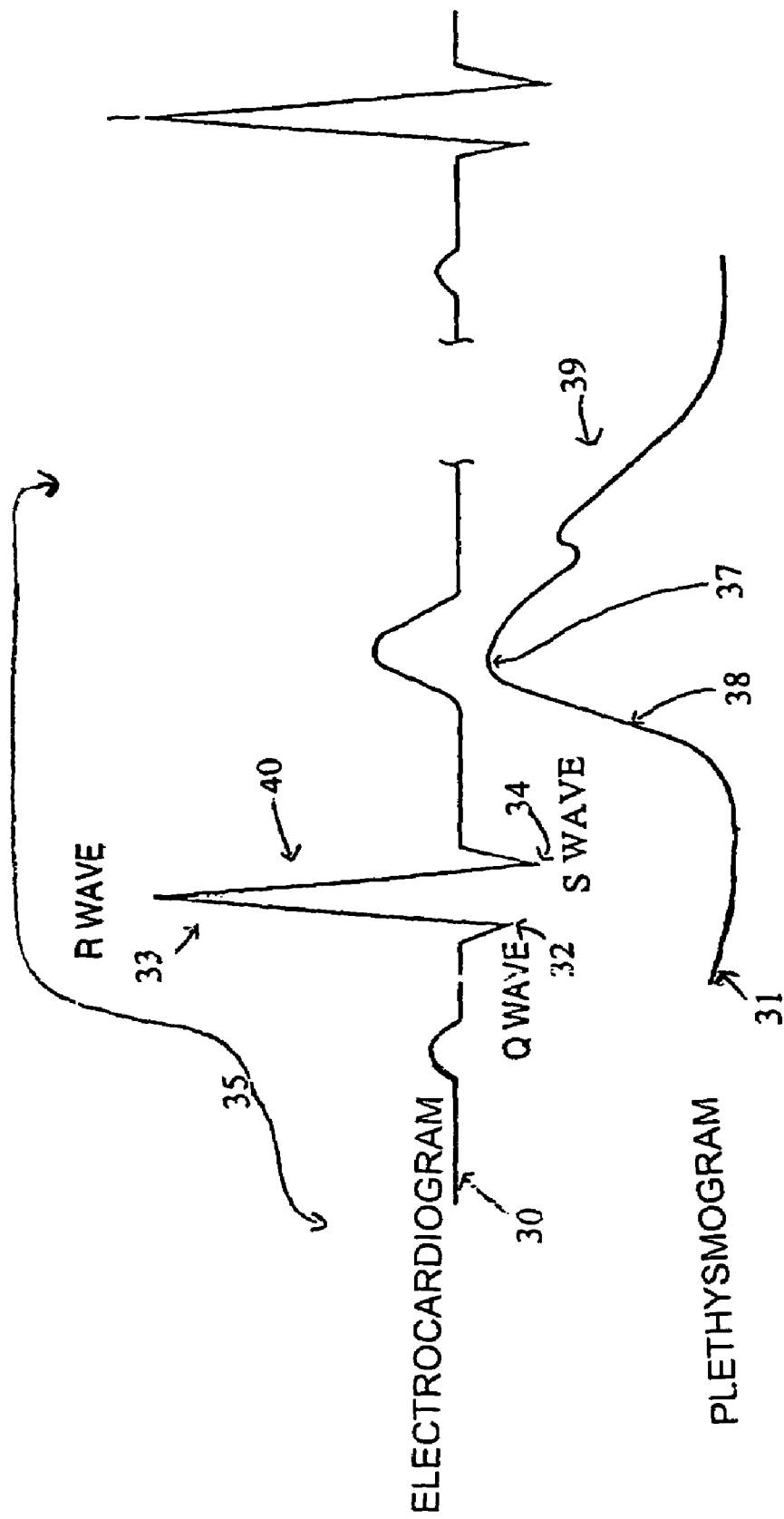
FIG. 2 illustrates an ECG waveform and a pulse oximeter waveform that are representative of a relationship between the two waveforms utilized by the present invention.

FIG. 2 illustrates an ECG waveform (electrocardiogram) 30 and a pulse oximeter waveform (plethysmogram) 31 that are substantially representative of the relationship between the two waveforms in real time. ECG waveform 30 comprises a first heartbeat 35, where first heart beat 35 comprises in part Q wave 32, R wave 33, and S wave 34, herein referred to as QRS wave 40. QRS wave 40 is representative of the electrical activity recorded during the contraction of the left ventricle. Plethysmogram 31 comprises a pulse 39, where pulse 39 in part comprises slope 38 and peak 37. In a healthy patient, the pulses of plethysmogram 31 and the QRS waves of ECG 30 will have a one-to-one relationship, where for every QRS wave 40 there will be a corresponding pulse 39. Pulse 39 will, in a normal healthy patient, also lag behind QRS wave 40 by several milliseconds, where for every QRS wave a corresponding pulse will follow closely behind due to the time lapse between the contraction of the left ventricle and the resulting pulse of blood reaching the capillary bed under the pulse oximeter probe.

Though ECGs and pulse oximeters monitor different patient parameters, electrical heart activity and blood oxygen saturation level, respectively, interrelations between the two may be used in analyzing patient data to increase the specificity of monitoring systems. When compared to one another, a clear one-to-one relationship is established between QRS waves and plethysmogram pulses. Furthermore, if a patient's heart experiences ventricular fibrillation, where ECG 30 will not display the standard QRS wave, plethysmogram 31 will generally show reduced or absent pulses. Likewise, if plethysmogram 31 detects reduced or absent pulses as a result of ventricular fibrillation, ECG 30 will show reduced or absent QRS waves. If abnormalities are presented by data from both monitors, it is highly likely that the data is indicative of a true patient condition and not the result of spurious data.

Based on the above illustrated connection, if ECG 30 monitoring a patient's heart condition becomes erratic, indicating possible ventricular fibrillation, but plethysmogram 31 indicates a normal level and number of pulses, it is highly likely that the ECG data is the result of, for example, clinician motion in the surgical field and not that of a potentially life-threatening situation. Similarly, if plethysmogram 31 displays an erratic waveform, potentially indicating ventricular fibrillation, but ECG 30 displays a healthy waveform, it is highly likely that the plethysmogram data is the result of, for example, poor placement of the pulse oximeter, and not that of a potentially life-threatening situation.

Still referring to FIG. 2, the present invention comprises integrating the analysis of related patient parameters such as, for example, electrical heart activity and pulse oximetry, where such analysis may diminish the probability of false positive alarm responses. For example, sedation and analgesia system 22, or any other suitable monitoring system, incorporating the sensor fusion of ECG and pulse oximetry, may analyze data from both monitors in order to ensure that data presented on each is depicting actual patient condition. Methods of incorporating sensor fusion into sedation and analgesia system 22 or any other suitable monitoring device or integrated delivery system are further disclosed herein, however, illustrated interrelated patient parameters are disclosed by way of example only, where any suitable patient parameter related to any other suitable patient parameter may be used in accordance with the present invention.

Figure 3:
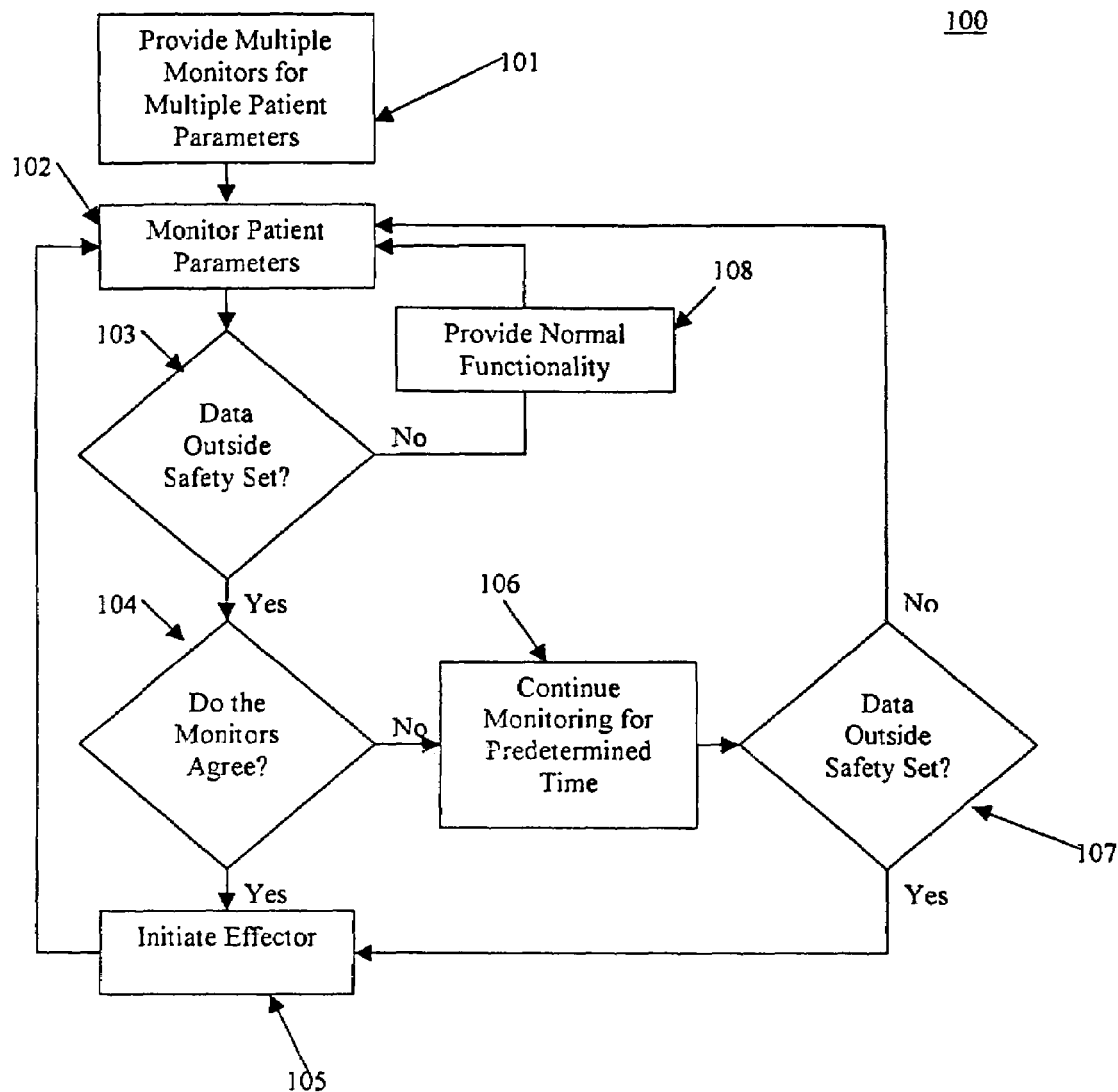
FIG. 3 illustrates one embodiment of a method for providing and using sensor fusion to reduce the probability of false positive alarms in accordance with the present invention.

FIG. 3 illustrates one embodiment of a method 100 for providing and using sensor fusion to reduce the probability of false positive alarms in accordance with the present invention. Step 101 comprises providing at least one patient monitor corresponding to a first patient parameter, such as electrical heart activity, and at least one patient monitor corresponding to a second patient parameter, such as pulse oximetry. The present invention comprises the use of any suitable number of patient physiological parameters that are interrelated, where any suitable number of monitors may be used to monitor each patient parameter.

Step 102 comprises monitoring at least two interrelated patient parameters where monitored data may be processed by controller 14, displayed on user interface 12, or otherwise manipulated to ensure patient safety. For example, an ECG waveform used to monitor electrical heart activity and a plethysmogram may be displayed in real time or near-real time for an attending clinician to verify that both waveforms are healthy and that the two correspond. While monitoring the multiple parameters of the patient, method 100 may proceed to query 103.

Query 103 comprises ascertaining whether any of the monitors being used are transmitting data indicative of a negative patient episode such as, for example, ventricular fibrillation. This ascertainment may be done by comparing data from each of the monitors against a safety data set, where the safety data set may be programmed into, for example, sedation and analgesia system 22, and may be based on normally accepted safe and/or unsafe patient parameter ranges, may be programmed by the clinician, or both. For example, ECG thresholds for R wave 33 (FIG. 2) may be established, where the ECG waveform must cross the threshold for controller 14 to register first heart beat 35 (FIG. 2) as a healthy heart beat, however, any suitable means of monitoring the health of heart activity is in accordance with the present invention. Similarly, thresholds may be established for plethysmogram 31 (FIG. 2), where pulse 39 (FIG. 2) must cross a given threshold to indicate sufficiency of pulse oximetry. Plethysmogram 31 may be evaluated by any other suitable means such as, for example by the slope 38 or peak 37 (FIG. 2) of pulse 39.

Still referring to query 103, if data presented by either of the monitors is not outside of the safety data set, method 100 may proceed to step 108. Step 108 comprises providing normal system functionality in the absence of alarms and/or other effectors designed to alert the attending clinician and recover a patient from a potentially harmful situation. If any of the monitors associated with step 101 indicate data outside of the safety data set, method 100 may proceed to query 104.

Query 104 comprises ascertaining whether the monitors of the associated parameters agree with one another, where each monitor transmits data indicative of a potentially harmful patient event. It may be determined that there is cause for alarm if, for example, ECG and pulse oximetry are being used, and the ECG and plethysmogram have a one-to-one relationship and are both registering below the required thresholds. In the case of ventricular defibrillation, both monitors will likely fail to meet such a threshold, indicating that the patient is probably experiencing a potentially life-threatening condition and that the data is not due to artifact. If the monitors agree that the monitored patient parameters indicate a potentially dangerous situation, method 100 may proceed to step 105.

Step 105 comprises initiating any suitable procedure to alert clinicians to the detected data indicating a negative patient event, as well as any automated or semi-automated procedure to place the patient into a safe state. For example, the effectors of step 105 include, but are not limited to, alarming, decreasing drug levels, delivering oxygen, changing drugs to, for example, an opioid antagonist, requesting the monitoring system, such as sedation and analgesia system 22, to gather more data, testing patient responsiveness, and/or delivering positive airway pressure. Such actions will likely have a high degree of specificity following query 104 due to the agreement between multiple monitors monitoring multiple patient parameters that are in agreement as to whether a potentially harmful patient condition exists. While step 105 is occurring, method 100 may continue to loop back to step 101, where patient monitoring may occur throughout the duration of step 105. Following a "no" response to query 103, method 100 may then return to the normal system operability of step 108.

Returning to query 104, the monitors of step 101 may be determined not to agree if, for example, one of such monitors falls below the threshold while the other does not. A lack of agreement may also arise if both monitors achieve the required thresholds, but do not maintain a one-to-one relationship with one another. Due to the relationship between the two monitored parameters, it is unlikely that, for example, the ECG will become erratic while the plethysmogram remains regular, and vice versa. In such events, it is therefore likely that the erratic monitor detecting a potentially critical patient event may have been subjected to motion disturbance, improper placement, or some other means of creating spurious data. To ensure patient safety yet retain high sensitivity during such situations, method 100 may proceed to step 106.

Step 106 comprises, in one embodiment of the present invention, continuing to gather data from the monitors associated with step 101 for a predetermined period of time, where no alarm or other effector action is taken. Often, discrepancies between the monitors will be cleared up as, for example, clinician motion in the surgical field stops. By providing a delay before moving to step 105 of, for example, 10 seconds, monitors that are erratic due to spurious data may regain normal function, thereby avoiding a false positive alarm due to such spurious data. Following step 106, method 100 may then proceed to query 107.

Query 107 comprises, in one embodiment of the present invention, reevaluating whether any of the monitors associated with step 101 indicate a negative patient condition. If, for example, the monitors still don't agree, but at least one remains outside of the safe data set, method 100 may transition to step 105. In one embodiment of the present invention, step 105 comprises a mild or warning alarm for those situations in which monitors don't agree, and a more emphatic or severe alarm for those circumstances in which both monitors register data outside of the safety data set. The present invention further comprises any suitable number of alarms employing any suitable effectors associated with step 105, where various effectors, such as mild or severe alarms, may be triggered based on various patient and monitor conditions. If, with respect to query 107, the data from the monitors no longer falls outside of the safety data set, method 100 may loop back to step 102. Method 100 may be terminated at any time by the attending clinician.

The method of FIG. 3 is illustrated by way of example only, where any suitable related patient parameters may be employed to increase the specificity of the monitoring system, such as sedation and analgesia system 22, by decreasing the probability of false positive alarms based on data artifact. Further, it is contemplated that safety data sets may vary for various patient parameters, where any suitable data set may be established for any suitable patient parameter in accordance with the present invention.

FIG. 4A illustrates one embodiment of a capnogram 50, where capnogram 50 illustrates a generally healthy carbon dioxide partial pressure waveform 55 based on partial pressure y-axis 54 and time axis 53. A healthy patient will generally have a period 51 of zero carbon dioxide output, where period 51 is attributable to inhalation and the early stages of exhalation. Period 51 will then generally be followed by a period 52 of carbon dioxide output, where period 52 is generally indicative of patient exhalation. A full respiratory cycle generally includes a first period 51 followed by period 52, where a normal patient will continue to breathe in such a pattern as indicated in FIG. 4A.

FIG. 4B illustrates a further embodiment of a capnogram 60 illustrating a carbon dioxide waveform 63 based on partial pressure y-axis 62 and time x-axis 61. Like FIG. 4A, FIG. 4B also displays a generally healthy carbon dioxide waveform 63, where a corresponding ventilatory pressure waveform 64 overlays carbon dioxide waveform 63. Ventilatory pressure waveform 64 is based on inhalation and exhalation pressure, where such pressures are related to the respiratory cycles that may be viewed with carbon dioxide waveform 63. As a patient begins to inhale, as illustrated in period 65, the patient will also display a period 66 of negative ventilatory pressure corresponding to the sub-ambient pressure caused by the patient's spontaneous respiratory effort. With period 67, indicative of patient exhalation, ventilatory pressure waveform 64 will display period 68, where period 68 is a period of positive (supra-ambient) ventilatory pressure caused by airflow expelled from the patient's respiratory tract.

FIG. 4B shows a connection between the patient parameters of capnometry and ventilatory pressure. As an example of sensor fusion, capnometry and ventilatory pressure may be used in accordance with method 100 in order to increase the specificity of monitoring systems such as, for example, sedation and analgesia system 22.

Figure 5A:
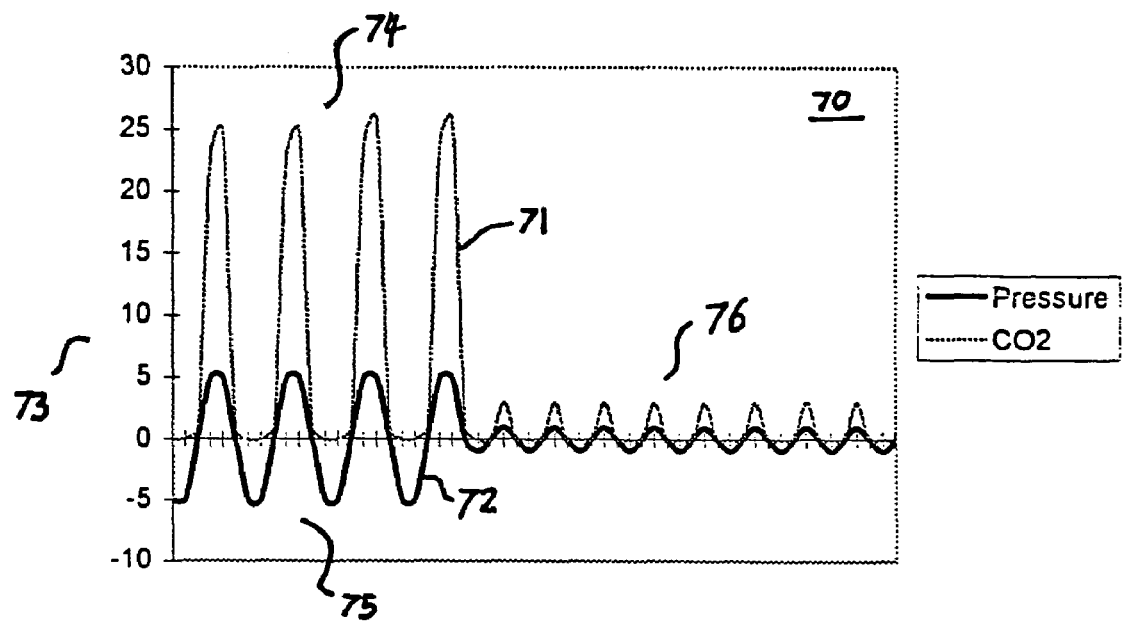
FIG. 5A illustrates an embodiment of a capnogram having a carbon dioxide partial pressure waveform overlaid with a ventilatory pressure waveform that is representative of data utilized by the present invention.

FIG. 5A illustrates a display 70 having carbon dioxide partial pressure waveform 71 overlaid with ventilatory pressure waveform 72. Data is plotted based on pressure y-axis 73 and an x-axis based on time. FIG. 5A further illustrates a period 74 of waveform 71 indicative of a healthy breathing patient correlated with period 75 of waveform 72. Periods 74 and 75 generally illustrate the interrelationship between capnometry and ventilatory pressure in a healthy patient. FIG. 5A further illustrates period 76, where period 76 is a period of low partial pressure carbon dioxide exhalations from the patient. If evaluated on the basis of data gathered from the capnometer alone, it is difficult to ascertain from waveform 71 alone whether the patient is experiencing hyperventilation or hypoventilation. As described above, both conditions will generally result in low carbon dioxide outputs; hyperventilation because of the shallowness of breath and hypoventilation because of the lack of adequate ventilation, often due to airway obstruction. Based on capnometry alone, monitoring systems would generally have to alarm if either condition occurs, even though hyperventilation is generally innocuous, in order to ensure that hypoventilation, a potentially life-threatening condition, was alarmed or alleviated. Alarming for both conditions based on inconclusive data will generally result in a high frequency of false positive alarms that decrease the sensitivity of monitoring systems such as, for example, sedation and analgesia system 22.

FIG. 5A therefore illustrates one embodiment of the present invention incorporating waveform 72 into the analysis of waveform 71, where data gathered from waveform 72 help to identify whether, for example, a capnograph is detecting hypoventilation or hyperventilation. FIG. 5A illustrates a situation where the patient is experiencing hypoventilation as can be seen by both a low level of output carbon dioxide as well as low ventilatory pressure, where hyperventilation is generally characterized by low carbon dioxide output and high ventilatory pressures. Based on the above analysis, a monitor system, such as sedation and analgesia system 22, could likely trigger an alarm response to the condition illustrated in FIG. 5A with a low probability of a false alarm and with high specificity.

Figure 5B:
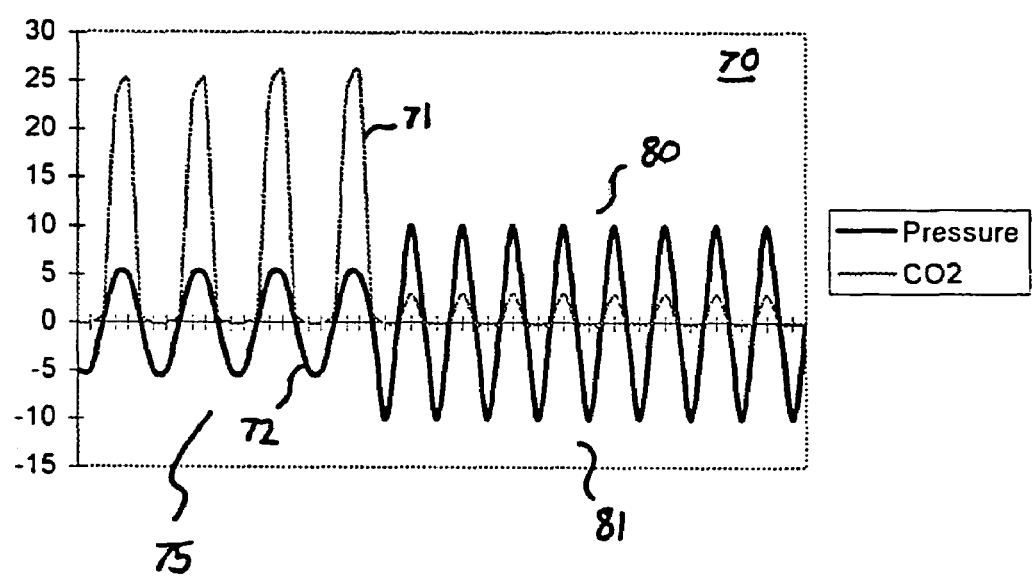
FIG. 5B illustrates a further embodiment of a capnogram having a carbon dioxide partial pressure waveform overlaid with a ventilatory pressure waveform that is representative of data utilized by the present invention.

FIG. 5B illustrates a further overlaid display 70, where FIG. 5B further includes period 80, where period 80 is a period of low partial pressure carbon dioxide exhalations from the patient. If evaluated on the basis of data gathered from the capnometer alone, it is difficult to ascertain from waveform 71 alone whether the patient is experiencing hyperventilation or hypoventilation. As described above, both conditions will generally result in lower carbon dioxide outputs: hyperventilation because of shallowness of breath and hypoventilation because of the lack of adequate ventilation, often due to airway obstruction. Display 70 further displays period 81 of waveform 72, where period 81 represents a series of pressure swings corresponding to period 80 of greater amplitude than those seen during period 75. Such an increase in amplitude of waveform 72 in view of the decrease in amplitude of waveform 71 during period 80 is generally indicative of hyperventilation. Since hyperventilation is generally an innocuous condition, the monitoring system, such as sedation and analgesia system 22, may by comparing the two data sets decide not to sound an alarm and/or initiate safety effectors because it has been determined that the data of FIG. 5B indicates hyperventilation.

By comparing separate but related patient parameters, the present invention functions to increase monitoring system specificity by reducing the number of false positive alarms associated with data artifact and inconclusive data. Providing such sensor fusion may reduce the number of false alarm states, where attending clinicians are more likely to trust the system when an alarm does sound. The illustrated concepts are disclosed by way of example only, where any suitable patient parameters having a relationship may be analyzed together to, for example, reduce false positive alarms due to artifact and/or inconclusive data.

Figure 6:
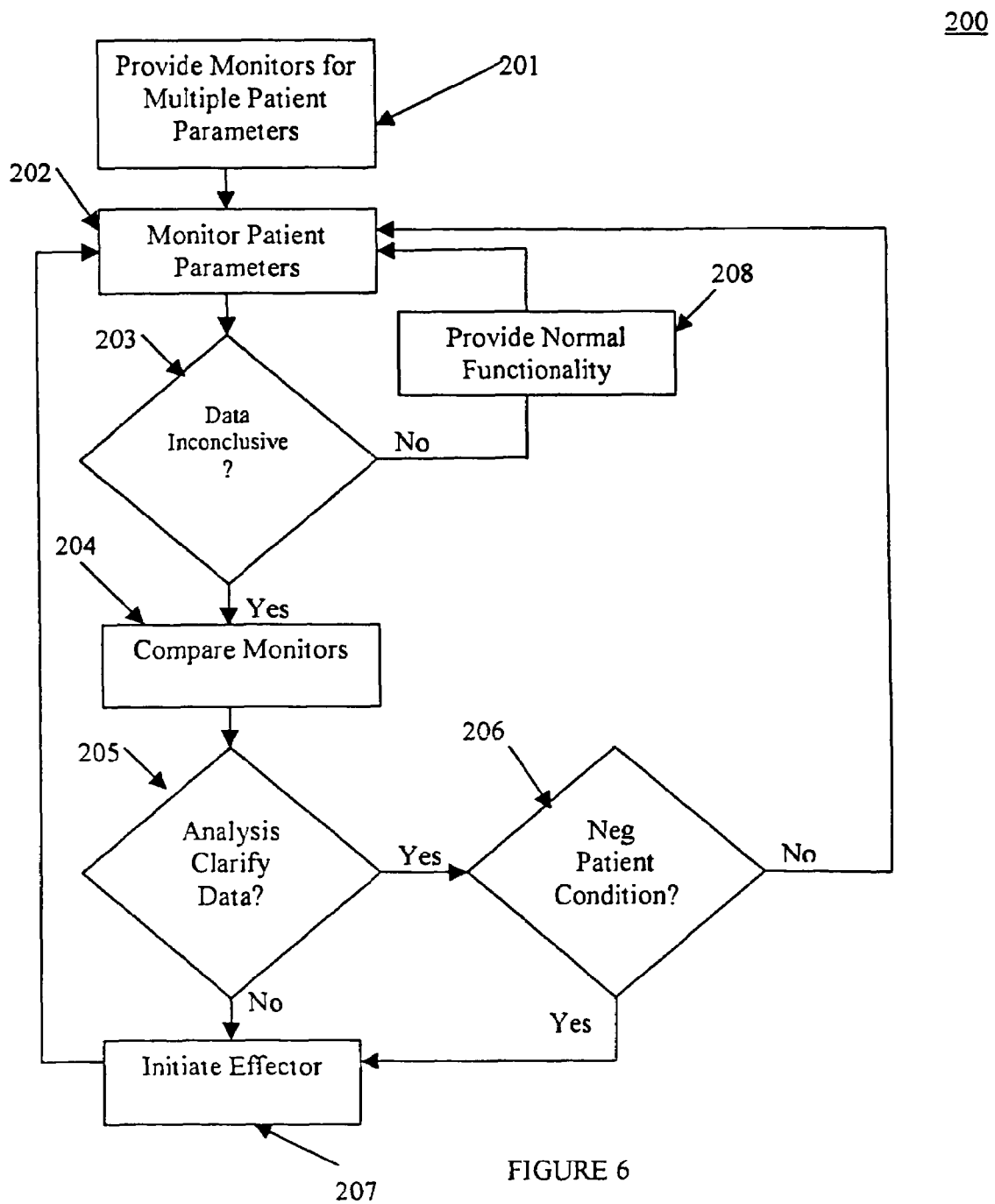
FIG. 6 illustrates one embodiment of a method for employing sensor fusion in accordance with the present invention.

FIG. 6 illustrates one embodiment of a method 200 for employing sensor fusion in accordance with the present invention. Step 201 of method 200 comprises providing at least one patient monitor corresponding to a first patient parameter, such as capnometry, and at least one patient monitor corresponding to a second patient parameter, such as ventilatory pressure. The present invention comprises the use of any suitable number of patient physiological parameters that are interrelated, where any suitable number of monitors may be used to monitor each patient parameter. Step 202 comprises monitoring at least two interrelated patient parameters where monitored data may be processed by controller 14, displayed on user interface 12, or otherwise be manipulated to ensure patient safety. For example, a capnogram used to monitor the partial pressure of expired carbon dioxide and a ventilatory pressure waveform may be displayed in real-time or near real-time for an attending clinician to verify that both waveforms are appropriate and that the two correspond.

While monitoring the multiple patient parameters of the patient, method 200 may proceed to query 203.

Query 203 comprises ascertaining whether the data from either of the monitors associated with step 201 is conclusive in and of itself. For example, a normal capnogram may not require the additional analysis of ventilatory pressure in order to ensure the accuracy or meaning of the capnogram. Further, a healthy capnogram is generally not indicative of inconclusive data. If such data is conclusive, method 200 may proceed to step 208, where step 208 comprises providing normal system functionality in the absence of alarms and/or other effectors designed to alert the attending clinician and/or recover a patient from a potentially harmful situation. From step 208, method 200 may continually loop back to step 202 in order to ensure continued patient safety.

Still referring to query 203, if data is inconclusive, as illustrated in FIGS. 5A and 5B, method 200 may proceed to step 204. Step 204 comprises comparing and analyzing the data from the interrelated patient parameters to determine whether one monitor can confirm or deny a potentially critical condition indicated by at least one other monitor. Such a comparison may be that illustrated in FIGS. 5A and 5B, or any other suitable comparison and analysis may be done by controller 14 or any other suitable programmable device or, for example, data from interrelated patient parameters may be presented to clinicians in order for them to make a determination based on a visual display.

Query 205 comprises ascertaining whether the inconclusive data was able to be clarified by the incorporation of data from an interrelated patient parameter. For example, such a clarification would exist in the circumstances of FIGS. 5A and 5B, where the use of a ventilatory pressure waveform clarifies an inconclusive capnogram. However, if monitors associated with step 201 are not able to clarify inconclusive data, such as if both monitors become erratic, method 200 may proceed to step 207.

Step 207 comprises initiating any suitable procedure to alert clinicians to the detected data indicating inconclusive data or a negative patient event, as well as any automated or semi-automated procedures desirable in placing the patient into a safe state. For example, the effectors of step 207 include, but are not limited to, alarming, decreasing drug levels, delivering oxygen, changing drugs to, for example, an opioid antagonist, requesting the monitoring system, such as sedation and analgesia system 22, to gather more data, testing patient responsiveness, and/or delivering positive airway pressure. Further, the present invention comprises providing different alarm modes in accordance with step 207, where the effectors of step 207 may vary depending on the cause of the transition to step 207 such as, for example, where a more severe alarm may be initiated for a "yes" response to step 206 than for a "no" response to step 205. During step 207, method 200 may continually loop back to step 202 to determine whether the monitors indicate healthy data and/or whether the patient condition has recovered.

Returning to query 205, if the analysis of data from multiple monitors is able to clarify inconclusive data, method 200 may proceed to query 206. Query 206 comprises ascertaining whether the clarified data is indicative of a negative patient condition based on, for example, a safe data set programmed into controller 14 (FIG. 1), where, for example, the negative patient event is one such as that illustrated in FIG. 5A. If such a negative condition is determined to exist, method 200 may proceed to step 207. If it is determined from the clarified data that no potentially dangerous patient condition exists, such as the condition of FIG. 5B, then method 200 may proceed to step 202. It is further noted that method 200 may be terminated or overridden at any suitable point by a clinician.

Method 200 may be integrated with method 100 (shown in FIG. 3), where interrelated patient parameters may be used to dismiss data artifact, clarify inconclusive data, or incorporate sensor fusion to otherwise ensure patient safety. Further embodiments of the present invention comprise integrating vascular turbulence power via a non-invasive blood pressure cuff with the slope of pulses monitored via pulse oximetry, where such an interrelation may provide redundant monitoring of the contractility of the heart. However, the present invention comprises the sensor fusion of any suitable monitors associated with any suitable interrelated patient parameters, where such an integration benefits patient safety.

Figure 7:
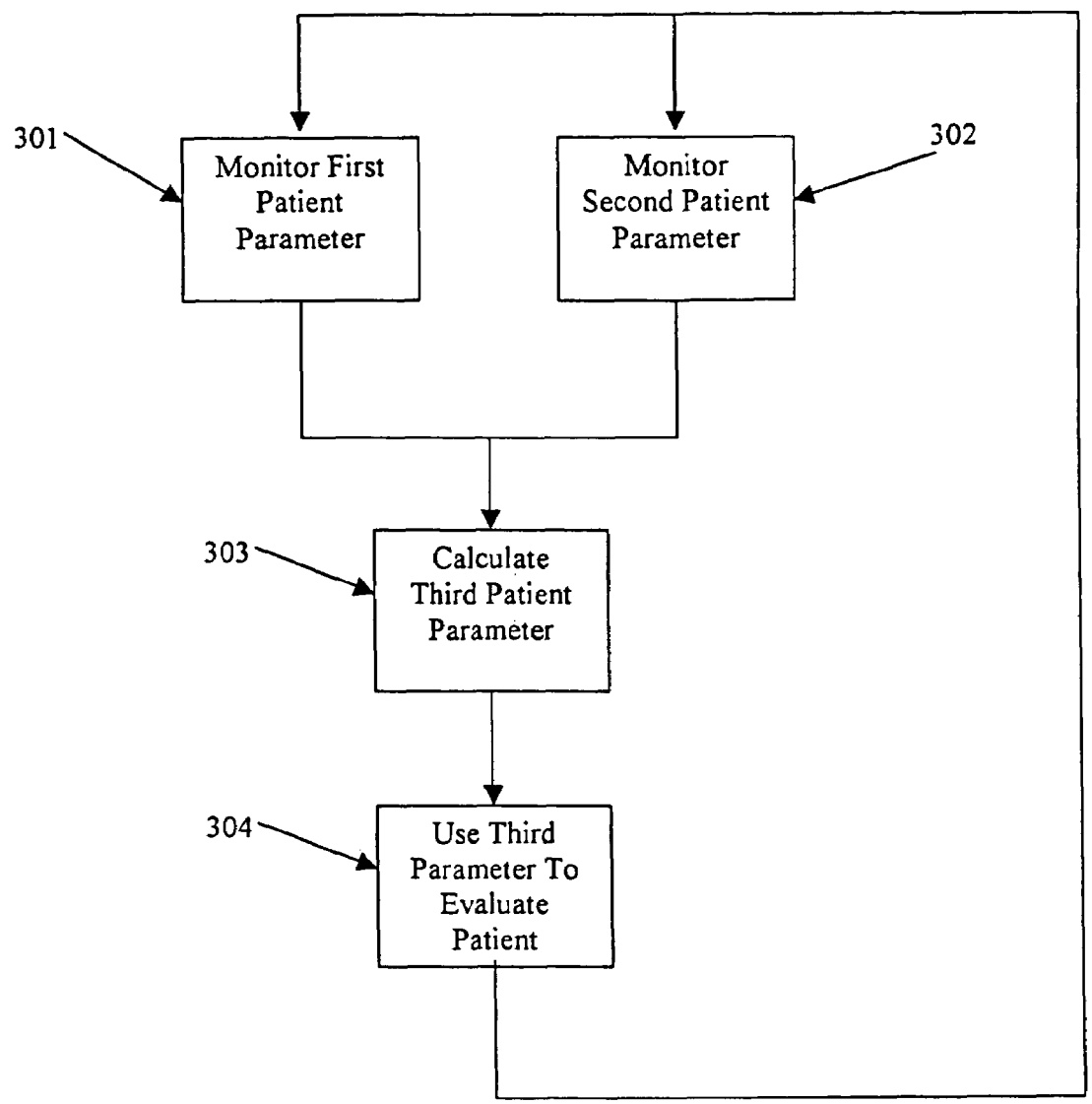
FIG. 7 illustrates one embodiment of a method for using multiple monitors of patient parameters that are easily monitored to calculate a third parameter that may be difficult to monitor in accordance with the present invention.

FIG. 7 illustrates one embodiment of a method 300 for using multiple monitors of patient parameters that are easily monitored to calculate a third parameter that may be difficult to monitor. Method 300 comprises step 301, where step 301 comprises monitoring a first patient parameter, such as mean arterial pressure, via a suitable patient monitor, such as a non-invasive blood pressure cuff. Step 302 comprises monitoring a second patient parameter, such as blood flow or perfusion, via a suitable patient monitor, such as by the plethysmogram of a pulse oximeter. In one embodiment of method 300, steps 301 and 302 occur throughout the duration of a medical procedure.

Method 300 further comprises step 303, where step 303 comprises using the data monitored from step 301 and step 302 to calculate a third patient parameter. For example, based on the formula for calculating blood flow:

$$\frac{P_1 - P_2}{R} = F$$

$P_1$ is representative of mean arterial pressure (MAP), $P_2$ is representative of mean vascular pressure (MVP), R is representative of systemic vascular resistance (SVR), and F is representative of flow, where it is desirable to calculate R by non-invasive means. Where, in accordance with step 301, MAP may be inferred from a non-invasive blood pressure cuff and, in accordance with step 302, F may be inferred based on the plethysmogram of a pulse oximeter. In one embodiment of the present invention, $P_2$ may be eliminated from the equation due to the negligible effect of MVP on the equation. Therefore, the following formula may be created for determining R (SVR):

$$\frac{MAP}{F} = R$$

Based on the illustrated equation, the present invention comprises computing the data gathered from a patient monitor, such as a non-invasive blood pressure cuff, indicative of MAP with data gathered from a second patient monitor, such as a plethysmogram derived from a pulse oximeter, in order to calculate the system vascular resistance of the patient. By combining the monitored patient parameters of step 301 and step 302, the present invention comprises calculating a third patient parameter, such as systemic vascular resistance, in accordance with step 303. The third parameter of step 303 may be computed by, for example, controller 14. By fusing the sensors associated with step 301 and step 302, the present invention is able to compute a third patient parameter that is difficult to measure in most medical procedures. Such parameters may have considerable value in evaluating patient condition as will be further discussed herein.

Step 304 comprises using the third parameter calculated in step 303 to monitor the patient, where the third parameter may be used as a patient parameter in accordance with method 100 (FIG. 3), with method 200 (FIG. 6), independently, or for any other suitable means. For example, if used in accordance with method 200, systemic vascular resistance may be used to clarify inconclusive blood pressure data. A patient experiencing, for example, an internal gastrointestinal bleed, will generally exhibit a gradual decrease in blood pressure followed by more pronounced drop in blood pressure, where the gradual decrease is the result of the body's maintaining blood pressure by constricting the systemic vasculature and the pronounced drop occurs when the constriction is no longer able to maintain blood pressure due to significant blood loss. In patients experiencing anaphylaxis, blood pressure conditions will appear similar to those displayed during a gastrointestinal bleed. Anaphylaxis is caused by an allergen that leads to mast cell degranulation that releases massive histamine, where such an allergic response generally results in a dramatic decrease in vascular resistance resulting in a gradual drop in blood pressure followed by a precipitous drop. From data based solely on blood pressure it may be difficult or sometimes impossible to discern if either of the two conditions are present. However, in the case of a gastrointestinal bleed, vascular resistance will rise markedly as constriction occurs, whereas in the case of anaphylaxis, resistance will drop due to the vascular dilation caused by histamines. Therefore, by analyzing blood pressure in cooperation with systemic vascular resistance, it may be possible to clarify data that might otherwise be inconclusive, where different effectors may be initiated depending on which, if either, condition exists.

Method 300 comprises computing any suitable parameter in accordance with step 303 based on the monitoring of any suitable parameters associated with steps 301 and 302. Method 300 further comprises any suitable number of patient monitors used to calculate the patient parameter associated with step 303, where such monitors may monitor any suitable number of patient parameters.

While exemplary embodiments of the invention have been shown and described herein, it will be obvious to those skilled in the art that such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope by the claims as they will be allowed.

The invention claimed is:

1. A patient monitoring system for a sedation and/or analgesia procedure, comprising:
    a first patient health monitor device adapted so as to be coupled to a patient and so as to generate a first signal reflecting a first parameter of a physiological condition of the patient;
    a second patient health monitor device adapted so as to be coupled to the patient and so as to generate a second signal reflecting a second parameter of a physiological condition of the patient, wherein said first parameter and said second parameter are interrelated such that said first and said second signal are indicative of a single patient condition associated with said sedation and/or analgesia procedure;

an electronic controller accessing safety parameters for each of said first and second physiological conditions operatively connected to said first and second patient health monitor devices, wherein the electronic controller compares said first and second parameters with said safety parameters so as to initiate a response upon detection of undesirable signals from both of said first and second patient health monitor devices so as to facilitate conservative application of sedative or analgesic drug delivery and/or other suitable effectors, wherein conservative application comprises maintenance or decrease of sedative or analgesic drug delivery, and wherein if the comparison of said first or second parameter with said safety parameters is inconclusive, the electronic controller provides normal system functionality without alerting clinicians while determining whether one patient health monitor device can confirm a potential condition indicated by the other patient health monitor device.

2. The patient monitoring system of claim 1, wherein said first and second patient health monitoring devices are each independently selected from the group consisting of non-invasive blood pressure monitors, pulse oximeters, capnometers, ECGs, patient consciousness assessment systems, ventilatory flow monitors, ventilatory pressure monitors, impedance plethysmographs (IPGs), gas analyzers, ventilatory temperature monitors, ventilatory humidity monitors, and acoustical monitors.

3. The patient monitoring system of claim 1, wherein said response comprises at least one of decreasing drug levels, delivering oxygen, changing drugs, testing patient responsiveness, and delivering positive airway pressure.

4. The patient monitoring system of claim 1, wherein said electronic controller further accesses a third patient parameter and comprises using the monitored data for the first patient parameter and the second patient parameter to calculate said third patient parameter that is compared against said safety parameters for said third patient parameter.

5. A method for employing sensor fusion in a sedation and analgesia system, comprising the following steps:
providing at least one patient monitor corresponding to a first patient parameter and at least one patient monitor corresponding to a second patient parameter, wherein said parameters are interrelated and each of said monitors provide data indicative of a single patient condition associated with use of said sedation and/or analgesia system;
monitoring at least two of said interrelated patient parameters;
ascertaining whether any of said data is indicative of a negative patient episode;
if any of said data is indicative of a negative patient episode, determining whether there is agreement between each monitor, or if any of said data is inconclusive, providing normal system functionality without alerting clinicians while determining whether one monitor can confirm a potential condition indicated by at least one other monitor; and
initiating a suitable procedure in response to said data indicative of a negative patient episode or confirmed potential condition so as to facilitate conservative application of sedative or analgesic drug delivery and/or other suitable effectors, wherein conservative application comprises maintenance or decrease of sedative or analgesic drug delivery.

6. The method of claim 5, wherein said step of ascertaining further comprises comparing said data from each of the monitors against a set of safety parameters.

7. The method of claim 5, wherein said suitable procedure comprises at least one of decreasing drug levels, delivering oxygen, changing said drugs supplied to the patient, testing patient responsiveness, and delivering positive airway pressure.

8. The method of claim 5, wherein said step of determining whether there is agreement between each monitor comprises comparing data from each of said monitors with a respective set of safety parameters.

9. The method of claim 8, wherein said step of determining whether there is agreement between each monitor further comprises evaluating the relationship between said data for said monitored parameters that fall within said set of safety parameters.

10. The method of claim 5, further comprising continuing to gather data from the monitors for a predetermined period of time before said suitable procedure is initiated.

11. The method of claim 5, wherein said first patient parameter comprises electrical heart activity and said second patient parameter comprises pulse oximetry.

12. The method of claim 5, further comprising after said monitoring step, the step of using the monitored data for the first patient parameter and the second patient parameter to calculate a third patient parameter.

13. The method of claim 12, wherein said step of ascertaining further comprises comparing said third patient parameter against a set of safety parameters.

14. A method for employing sensor fusion in a drug delivery system during delivery of a sedative and/or analgesic drug, comprising the following steps:
providing at least one patient monitor corresponding to a first patient parameter and at least one patient monitor corresponding to a second patient parameter, wherein said parameters are interrelated and each of said monitors provide data;
monitoring at least two of said interrelated patient parameters,
ascertaining whether the data from any of said monitors is conclusive of a potentially critical condition;
if data is inconclusive, providing normal system functionality without alerting clinicians while analyzing the data from said first and second patient parameters to determine whether one monitor can confirm the potentially critical condition indicated by at least one other monitor; and
if data is conclusive of a potentially critical condition, alerting clinicians to the detected data and initiating a suitable automated or semi-automated procedure desirable to place the patient into a safe state.

15. The method of claim 14, wherein said data is processed by a controller.

16. The method of claim 15, further comprising the step of ascertaining whether the clarified data is indicative of a negative patient condition based on a set of safety parameters programmed into the controller.

17. The method of claim 14, wherein said suitable procedure comprises at least one of decreasing drug levels, delivering oxygen, changing said drugs supplied to the patient, and delivering positive airway pressure.

18. The method of claim 14, wherein said step of alerting clinicians comprises providing different alarm modes that vary depending on whether the data inconclusively or conclusively indicates the potentially critical condition.

19. The method of claim 14, wherein said first patient parameter comprises capnometry and said second patient parameter comprises ventilatory pressure.

20. The method of claim 14, further comprising after said monitoring step, the step of using the monitored data for the first patient paramater and the second patient parameter to calculate a third patient parameter.

21. The method of claim 20, comprising integrating blood pressure data with pulse oximetry data, where such an interrelation may provide monitoring of the systemic vascular resistance.

* * * * *